United States Patent
Brawn

[11] 3,977,399
[45] Aug. 31, 1976

[54] POSITIVE PRESSURE AND VOLUME MEASURE RESPIRATORY DEVICE

[76] Inventor: Peter Nelson Brawn, 36 Fairfield St., Pittsfield, Mass. 01201

[22] Filed: Apr. 15, 1975

[21] Appl. No.: 568,378

Related U.S. Application Data

[63] Continuation-in-part of Ser. No. 476,699, June 5, 1974, abandoned.

[52] U.S. Cl. ............................... 128/2.08; 272/99
[51] Int. Cl.² ........................................... A61B 5/08
[58] Field of Search ............... 128/2.08, 2.07, 2 C, 128/24 R, 25 R, 28, 30, 145.6, 145.7; 272/57 F, 99; 73/219, 222

[56] References Cited
UNITED STATES PATENTS

| | | | |
|---|---|---|---|
| 714,141 | 11/1902 | Cady | 128/2.08 |
| 3,710,780 | 1/1973 | Milch | 272/57 F |
| 3,811,671 | 5/1974 | Turnbull | 128/2.08 |

FOREIGN PATENTS OR APPLICATIONS

| | | | |
|---|---|---|---|
| 814,021 | 9/1951 | Austria | 128/2.08 |
| 640,590 | 7/1928 | France | 128/28 |
| 757,395 | 12/1933 | France | 272/57 F |
| 18,558 | 4/1963 | Japan | 128/2.08 |

*Primary Examiner*—Robert W. Michell
*Assistant Examiner*—Lee S. Cohen
*Attorney, Agent, or Firm*—Finnegan, Henderson, Farrabow & Garrett

[57] ABSTRACT

A novel positive pressure and volume measurement respiratory device is disclosed which provides positive pressure respiratory therapy to the user. Simultaneously the user's inspiration volume can be measured by merely observing the amount of liquid displaced from one container to another. The respiratory therapy device is comprised of two containers connected by flexible tubing which are raised and lowered relative to one another by appropriate linkage connected to a motor either cyclically or intermittently dependent upon the needs of the user. A user tube which communicates with the interior of one container acts as the conduit to the mouth of the user for expelled air when positive pressure is developed within the container.

8 Claims, 12 Drawing Figures

3,977,399

POSITIVE PRESSURE AND VOLUME MEASURE RESPIRATORY DEVICE

BACKGROUND OF THE INVENTION

This application is a continuation-in-part application of Ser. No. 476,699, filed June 5, 1974 and now abandoned.

The invention disclosed in this application relates to apparatus used for respiratory therapy. More specifically, it provides automatic positive respiratory therapy for a patient by means of a relatively simply constructed and operated device.

Respiratory therapy is often necessary for post-operative patients and those with atelectasis, pneumonia, chronic bronchitis and emphysema. Various therapy devices have long been known in the art for encouraging deeper respiratory inhalation and exhalation. Most such devices use compressors and complicated electric control systems to provide regular positive inspiration or expiration therapy to the user.

In a previously filed application, Ser. No. 446,165, filed on Feb. 27, 1974 by the present inventor, a respiratory therapy system utilizing two containers filled partially with a liquid was disclosed. The system disclosed therein can be used either to encourage inspiration or expiration by the patient thereby providing respiratory therapy. However, it does not operate to provide automatic and cyclical positive expiration or inspiration for the patient. Positive here means a positive pressure in relation to the atmospheric pressure.

The present invention, without using complicated system provides an automatic and cyclical system through which positive pressure is produced to provide inspiration or expiration therapy for the patient while simultaneously allowing the patient to measure the volume of air inhaled or exhaled.

SUMMARY OF THE INVENTION

The present invention allows the patient to receive respiratory therapy by means of an automatic positive pressure apparatus. In accordance with the purpose of the invention, as embodied and broadly described herein, the positive pressure and volume measurement device of this invention comprises first and second containers for holding liquid, an interconnecting tube which can conduct liquid from one container to the other, a motor connected to raise and lower one container relative to the other, and a user tube adapted to fit in the user's mouth which projects through an upper wall portion of one container. The raising and lowering of the two containers relative to one another effect positive and negative pressures alternately in the container having the user tube. Thus when the container having the user tube is in the lower position of the two containers air is expelled through the user tube from the container as liquid is transferred and inspiration occurs. When the container is higher, liquid is withdrawn and the negative pressure draws air into the container through the user tube.

DESCRIPTION OF THE PREFERRED EMBODIMENTS

Figure 1:
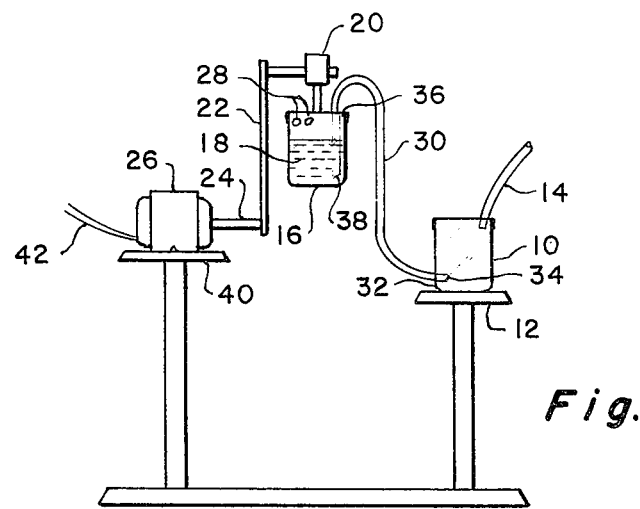
FIGS. 1, 2 and 3 show a schematic representation of a preferred embodiment of the present invention.
Figure 2:
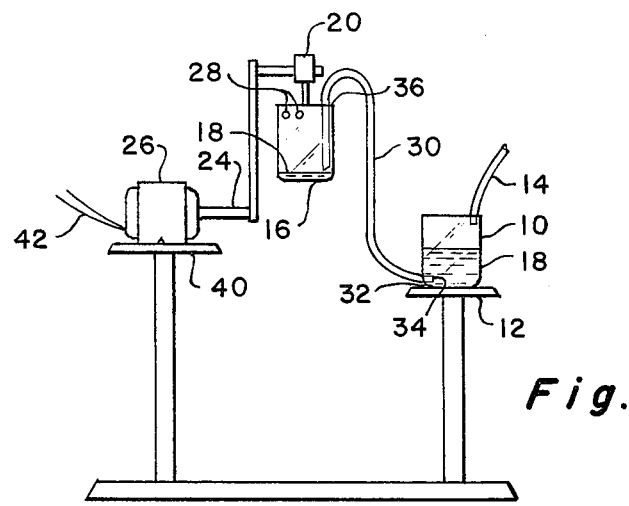
Figure 3:
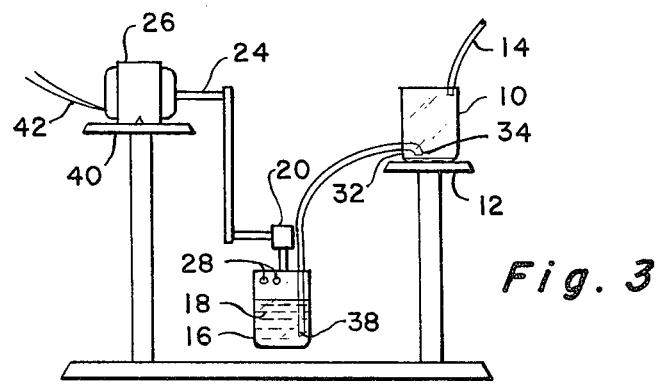

Referring now to the drawings and specifically to FIGS. 1, 2 and 3, there is shown a positive pressure and volume measurement respiratory device.

A first container 10 for holding a liquid is located in a stationary position on platform 12. Preferably the first container 10 has a user tube 14 which projects through an upper wall portion of the container 10. The user tube 14 is adapted to fit in a patient's or user's mouth. It is preferred that the user tube 14 be flexible and thin walled made of a suitable material such as plastic.

A second container 16 holding liquid 18 is supported from a swivel type connection 20 which is mounted on a top portion of the container 16. Through arm linkage 22 connected to the swivel type mounting 20, the container 16 is connected to the output shaft 24 of motor 26. When the output shaft of motor 26 rotates as shown the container 16 moves in an arc centered on the longitudinal axis of the shaft 24.

It is preferred that container 16 have one or more openings 28 in an upper wall portion thereof. The openings 28 communicate substantially atmospheric pressure to the surface of liquid 18 in container 16.

Means here embodied as motor 26 are operatively connected to the container 16 for raising and lowering the container 16 relative to the first container 10.

It is also preferred that flexible tubing 30 connect the first container 10 to the second container 16. As here embodied the flexible tubing 30 projects through a bottom container wall portion 32 into container 10 so that the end 34 of tubing 30 is located substantially at the bottom of the container 10.

Flexible tubing 30 projects through an upper container wall portion 36 into container 16 and end 38 of tubing 30 is substantially located at or near the bottom of container 16.

As here shown the motor means 26 is located on platform 40 and is normally connected to a power source by connection 42.

The operation of the positive pressure and volume measurement respiratory device is best described by reference sequentially to FIGS. 1, 2 and 3. Each of these figures shows a subsequent step in a cycle of operation of the respiratory device.

At the beginning of the operation, the total amount of liquid in the two containers 10 and 16 and tubing 30 should be less than half of the total volume of the two containers combined. If more liquid is used, the patient or user will likely inhale some liquid or upon an exhalation effort blow liquid out of the first container 10.

In FIG. 1, the second container 16 is shown in a raised position relative to container 10. The container 16 is substantially filled with liquid 18 while the first container 10 is substantially empty of liquid. At this point in the operation of the respiratory device, an inspiratory effort at the user tube 14 is required to start liquid movement from the higher container 18 to the lower container 10. Once liquid begins to move, the flow will continue by means of a siphon effect — that is the pressure on the surface of the liquid 18 in the container 16 will be greater than the pressure on the liquid entering container 10 due to the raised position of the second container 16. The specific pressure is determined by the difference in height between the containers and of course the difference can be increased or decreased to increase or decrease the pressure correspondingly. No further inspiratory effort is required by the user once the liquid begins to flow and a positive pressure is thereby created in container 10 causing air to be displaced from container 10 through the user tube 14. The positive pressure causes inspiration of air into the lungs of the user through the user's mouth.

In FIG. 2, all the liquid has been transferred from the second container 16 to the first container 10. The container 16 is still in a raised position relative to the first container 10, the motor 26 of this embodiment being operative intermittently either manually or automatically to raise and lower the second container 16. It will be understood however that a constant speed motor can be used to move container 16 through a complete revolution in a time equivalent to one breathing cycle of the user. In such a case, however, the positive pressure created between the two containers will vary with the speed of revolution since the difference in altitude between the containers will be in constant change and the device may not operate quite as efficiently as here shown.

The positive pressure created in the first container 10 is determined by the altitude difference between the two containers 10 and 16. Positive pressure may be increased in container 10 by increasing the distance between the two containers such as by increasing the length of the connecting linkage 22. Whereas the pressure is determined by the differences in altitude between the containers, the rate of flow of the liquid from one container to the other container is determined by (1) the diameters of the connecting tubing 30 and the user tubing 14 and (2) the number and size of the openings 28 in the upper wall portion of container 16. Either of these factors may be determinative of the rate of flow of the liquid. Thus if the diameter of the interconnecting tubing 30 is significantly smaller than the diameter of the user tubing 14 it will provide more restriction to flow thereby determining the rate of flow of the liquid. Additionally, if the holes in the upper portion of the second container 16 are few in number and small in size, the air flow into the container 16 may be restricted thereby reducing the flow rate of liquid out of container 16.

In FIG. 3, the second container 16 is positioned lower than the first container 10. The shaft 24 of the motor 26 has substantially moved through one half revolution hereby lowering the second container 16. With the connecting tubing 30 entering the first and second containers 10 and 16 as shown in FIG. 3, the liquid will flow automatically from container 10 to container 16 when container 16 is in the lowered position. No effort is required on the part of the user to initiate the flow of liquid. Motor 26 then continues rotation and the container 16 now substantially filled with liquid is raised to its previous higher position as shown in FIG. 1 and the cycle is repeated.

Motor 26 as previously stated can be rotated at any speed either continuously or intermittently. A schedule of operation of motor 26 can be established by the patient or doctor dependent on the patient's needs. A schedule may be either preset so that the motor operates automatically to control the cycle of breathing exercise or it may be controlled manually as through switching the motor on and off by the patient himself.

An accurate measurement of the inspiratory volume of the user can be determined by measuring the volume of fluid which is transferred from the second container 16 to the first container 10 as the user inhales from the user's tube 14. By substituting larger or smaller containers the needs and requirements of the user may be satisfactorily accomodated. Thus as a patient may require additional deep breathing exercise, larger containers and greater amounts of liquid can be used in the device. The positive pressure created during operation will transfer greater amounts of liquid and the user will necessarily increase the capacity of the air taken in.

In FIGS. 4A, 4B, 4C and 4D, there are shown schematically different preferred connections of the flexible tubing between the first and second containers of the present invention. Specifically in these embodiments the connections between the containers are shown for a system in which the user tube is inserted in the stationary container.

Figure 4A:
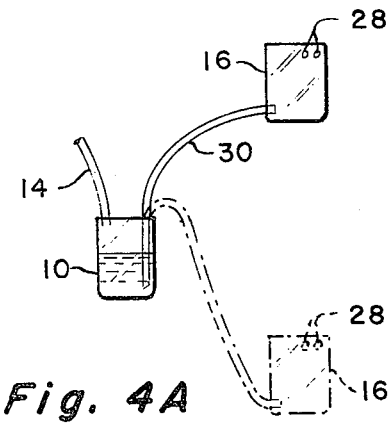
FIGS. 4A, 4B, 4C and 4D, show alternative tube connections to the containers of the present invention.

In FIG. 4A, the liquid flows automatically from the second container 16 to the first container 10 when container 16 is in a raised position. No inspiratory effort is required on the part of the user to initiate the flow of liquid. Consequently the positive pressure and resulting inspiration on the part of the user is automatic when the container 16 moves into the raised position. When container 16 is in the lower position, expiratory effort on the part of the user at the user tube 14 of container 10 is required to initiate flow of liquid from container 10 to container 16. Once initiated the flow of liquid continues until substantially all the liquid is transferred to container 16 through a siphon type action.

Figure 4B:
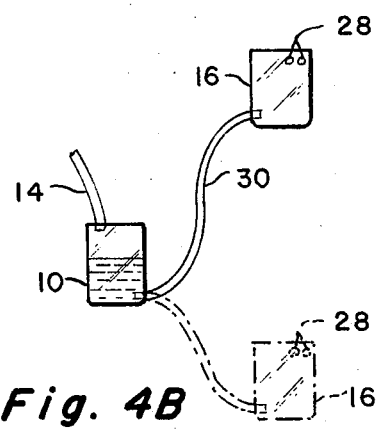

In FIG. 4B, the connecting tube 30 enters the respective containers 10 and 16 through lower container wall portions of each. Liquid then flows automatically from container 16 to first container 10 when the second container 16 is in a raised position relative to container 10. No inspiratory effort is required on the part of the user applied to the user tube 14 to initiate the flow of liquid. Consequently, the positive pressure is automatically developed, expelling air from container 10 through the user tube into the mouth and lungs of the user. Once the second container 16 is lowered liquid flows once again automatically from container 10 to container 16. No additional respiratory effort is required on the part of the user.

The embodiment of FIG. 4b is particularly appropriate when it is not desired to require the patient to initiate the positive pressure action but rather it is desired that the entire cycle operate automatically without patient involvement.

Figure 4C:
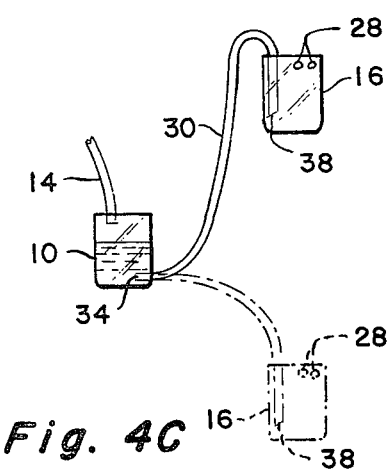

Now with reference to FIG. 4C, there is shown the connecting flexible tubing 30 projecting through a lower wall portion of the first container 10 and through an upper wall portion of second container 16. The respective ends 34 and 38 of flexible tubing 30 project into the respective containers to a point substantially at or near the bottom of each container. With this arrangement of containers and connecting tubing, a inspiratory effort must be applied to the user tube 14 by the user to initiate flow of liquid from container 16 to container 10 when container 16 is in a raised position. When container 16 having been emptied of liquid is moved to the lowered position, liquid flows automatically from the first container 10 to the second container 16. No additional respiratory effort is required of the user to effect transfer of liquid.

Figure 4D:
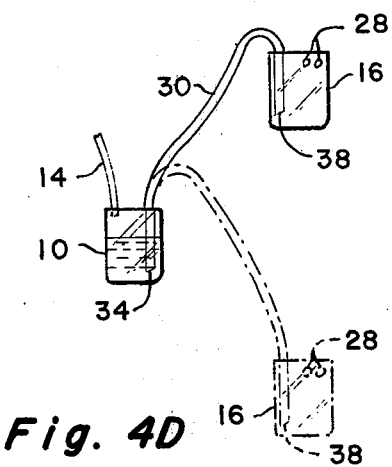

In FIG. 4D, the connecting flexible tubing 30 projects through respective upper wall portions of the first and second containers 10 and 16. Again, the respective ends 34 and 38 of the tubing 30 project to a point substantially at or near the bottom of each respective container. Inspiratory effort is required of the user to initiate a flow of fluid from the second container 16 to the first container 10 when container 16 is in the raised position. An expiratory effort by the user applied to the user tube 14 is required to initiate flow of liquid from container 10 to container 16 when container 16 has been lowered below container 10. Thus with the particular arrangement as shown in FIG. 4D, both an initial inspiratory effort and an initial expiratory effort is required on the part of the user to initiate the positive pressure action which transfers the liquid from one container to the other.

In each of the arrangements shown in FIGS. 4A, 4B, 4C and 4D, flow of liquid from the second container 16 to the first container 10 creates a positive pressure within the first container 10. This positive pressure forces air out of the container 10 through the user tube 14 to the user's mouth and lungs. Of course, the patient is never forced to breathe entirely from the user tube 14. However, as long as the user is motivated to use the device properly, the air forced from the first container 10 will be inhaled by the user thereby providing respiratory therapy.

Now referring to FIGS. 5A through 5D, various arrangements of the first and second containers and the flexible connecting tubing are shown where the first container having the user tube mounted thereon is moved relative to the second container. It will be readily apparent that the same general principles apply as explained in connection with FIGS. 4A through 4D. Basically it is the difference in altitude between the two containers which creates the positive pressure which causes the flow of liquid from one container to the other, and the point of entrance of the flexible tubing into each container determines whether that flow will be automatic or require a respiratory action by the user to initiate it. The principle of operation is not effected by which container is moved or even if both are moved relative to one another.

Figure 5A:
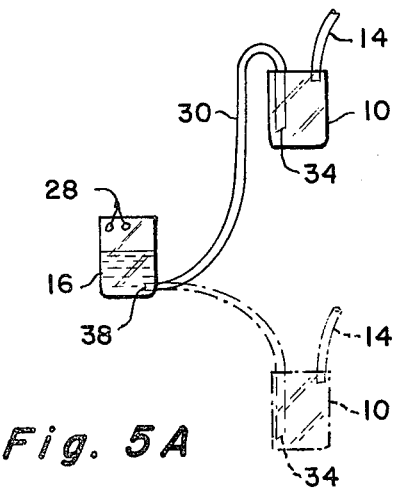
FIGS. 5A, 5B, 5C and 5D show further alternative tube connections to the containers of the present invention.

The arrangement of containers shown in FIG. 5A operate in a manner similar to that of the arrangement shown in FIG. 4A except that container 10 moves relative to stationary container 16. When the first container 10 is in a raised position relative to the second container 16 an expiratory effort applied to the user tube 14 is required to initiate a flow of liquid from the first container to the second container 16. On the other hand when container 10 is lowered to a position below container 16, flow of liquid from container 16 to container 10 is automatic and creates a positive pressure within container 10. This positive pressure causes air to be expelled from container 10 through the user tube 14 to the user.

Figure 5B:
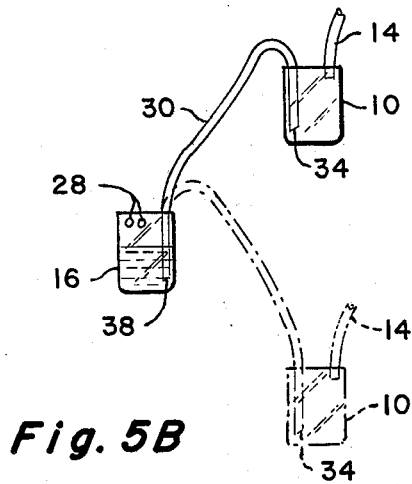

In FIG. 5B the transfer of liquid from one container to the other acts in a way similar to that of FIG. 4D except container 10 moves relative to stationary container 16. That is an expiratory effort on the part of the user applied to user tube 14 is required to initiate flow of liquid from container 10 when in a raised position relative to container 16. However, when container 10 is moved to a lowered position relative to the second container 16 an inspiratory effort by the user applied to the user tube 14 is needed to begin the flow of liquid from container 16 to container 10. Once the flow begins, a positive pressure is created in container 10 forcing air out through user tube 14 to the user.

Figure 5C:
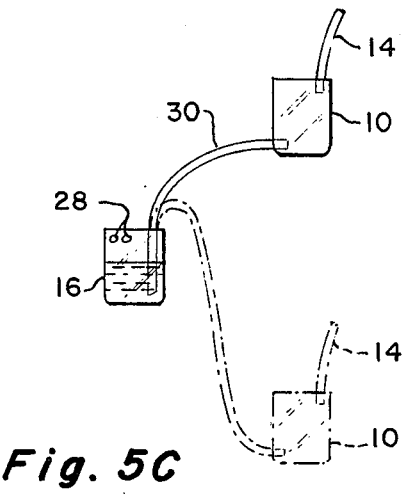

The arrangement of containers 10 and 16 and connecting tube 30 shown in FIG. 5C operates similarly to the particular arrangement shown in FIG. 4C. When the first container 10 is in the raised position relative to the second container 16 liquid automatically flows from container 10 to container 16 with no respiratory effort required on the part of the user. When container 10 is moved to a lowered position relative to container 16, an inspiratory effort by the user applied to the user tube 14 is required to initiate flow of liquid from container 16. Once started the flow into container 10 through tube 30 creates a positive pressure within the container which causes air to be expelled through user tube 14 to the user.

Figure 5D:
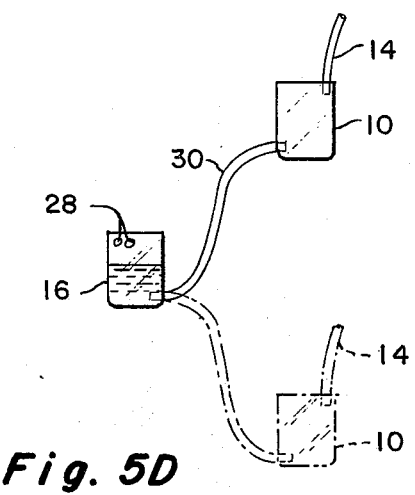

Finally, with regard to FIG. 5D, the arrangement shown operates in a manner similarly to that of the device of FIG. 4B. Thus, when container 10 is in a raised position relative to container 16, the liquid will automatically flow to the lower container 10. When the first container 10 is lower relative to the second container 16, liquid will automatically flow from container 16 to container 10, thereby creating a positive pressure which expels air from container 10 through user tube 14 to the user. The particular arrangement of containers and connecting tubing shown in FIG. 5D is such that no initiating respiratory action on the part of the user is required to cause the device to operate during any part of the cycle.

Figure 6:
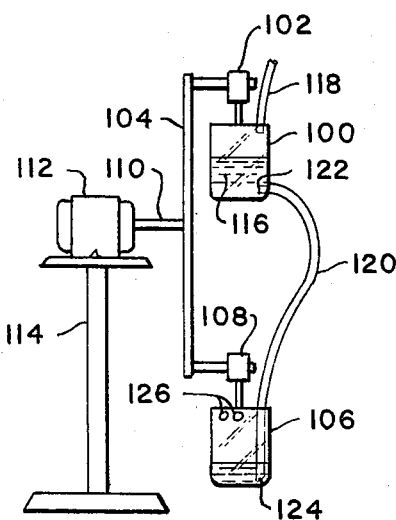
FIG. 6 shows a schematic representation of an alternative embodiment of the present invention.

FIG. 6 shows schematically another method of moving the first and second containers up or down relative to one another. As here embodied both containers are attached at the respective ends of a rotating arm member 104.

Preferably a first container 100 is mounted by means of a swivel mechanism 102 to one end of an arm assembly 104. A second container 106 is mounted to a similar swivel mechanism 108 at the other end of the arm assembly 104. The arm assembly is pivotally attached at the center thereof to the output shaft 110 of a motor 112. Suitable support means such as stand 114 is provided for the means such as stand 114 is provided for the motor 112. The swivel mechanisms 102 and 108 allow the containers 100 and 106 respectively freedom to remain oriented upright as the arm assembly 104 rotates.

The first container 100, holding liquid 116 has a user tube 118 projecting through an upper wall portion thereof and communicating with the interior of container 100. The user tube preferably is made of a flexible thin walled material.

A flexible connecting tube 120 connects the first container 100 to the second container 106. The connecting tube 120 exits the first container 100 from a bottom wall portion thereof. The end 122 of flexible tube 120 is located at or substantially near the bottom of container 100. Flexible tube 120 enters the second container 106 through an upper wall portion thereof. The second end 124 of tubing 120 is located at or substantially near the bottom of container 106.

Preferably second container 106 has one or more openings 126 in an upper portion of the container wall. The openings 126 communicate substantially atmospheric pressure to the interior of container 106.

By the rotation of output shaft 110 of motor 112, the first and second containers 100 and 106 can be raised and lowered relative to one another. Motor 112 can be programed to operate at a given continuous output speed or it can be scheduled to operate intermittently. Such operation can be attained either automatically or manually.

In the particular embodiment of FIG. 6, the user tube 118 is mounted in the container 100 which is periodically rotated. It will be recognized that the user tube 118 will necessarily have to have sufficient length and flexibility to allow movement of the container 100 without discomforture for the user or interruption of the system movement. With the use of flexible tubing such is easily attained.

It will be recognized that various types of motive means may be used to raise and lower one container relative to the other. For instance in place of a motor operative to create rotary motion motor with proper cam linkage can be used to simply raise and lower one container in a linear manner.

I claim:

1. A positive pressure and volume measurement respiratory device for use with liquid comprising:
   a first container for holding liquid,
   a second container for holding liquid,
   flexible tubing means for connecting the interior of said first container to the interior of said second container, the open ends of said flexible tubing means being positioned substantially near the bottom of each respective container,
   means operatively connected to at least one of said containers for raising and lowering said one container higher and lower than, respectively, the other container,
   a user tube affixed to an upper wall portion of said first container and communicating with the interior of said first container, said tube adapted to fit in the user's mouth,
   said second container having at least one opening in an upper wall portion thereof for communicating substantially atmospheric pressure to said liquid, and
   said raising and lowering means being operative to cycle said second container alternatively between positions respectively higher and lower than said first container to effect transfer of liquid between said containers thereby effecting a positive pressure at said user tube during transfer of liquid from said second container to said first container and a negative pressure at said user tube during transfer of liquid from said first container to said second container.

2. The device as defined in claim 1 wherein said first container is stationary.

3. The device as defined in claim 2 wherein said flexible tubing means projects through a lower wall portion of said first container and projects through an upper wall portion of said second container.

4. The device as defined in claim 1 wherein said first container is stationary and said raising and lowering means is operatively connected to said second container to rotate said second container through a path including points where said second container is relatively higher than and relatively lower than said first container.

5. The device as defined in claim 1 wherein said first container is stationary and wherein said raising and lowering means is operatively connected to said second container to impart a linear motion to said second container which raises and lowers said second container to points higher and lower respectively than said first container.

6. The device as defined in claim 1 wherein said raising and lowering means includes a motor, an output shaft connected to said motor, and a linkage arm assembly having a first end fixidly attached to said shaft and a second end swivelly attached to said second container.

7. The device as defined in claim 1 wherein said raising and lowering means is connected to said first container for raising and lowering said first container with respect to said second container.

8. The device as defined in claim 1 wherein said raising and lowering means is connected to said first and second container.

* * * * *